United States Patent [19]
Johnson

[11] Patent Number: 5,452,091
[45] Date of Patent: Sep. 19, 1995

[54] SCATTER CORRECTION IN REFLECTIVITY MEASUREMENTS

[75] Inventor: Rodney P. Johnson, Milpitas, Calif.

[73] Assignee: Nanometrics Incorporated, Sunnyvale, Calif.

[21] Appl. No.: 35,291

[22] Filed: Mar. 22, 1993

[51] Int. Cl.⁶ .......................... G01N 21/55; G01J 3/28
[52] U.S. Cl. .................................. 356/445; 356/326; 356/381; 356/448
[58] Field of Search ................ 356/445, 448, 326, 381

[56] References Cited

U.S. PATENT DOCUMENTS

| | | | |
|---|---|---|---|
| 4,350,442 | 9/1982 | Arild et al. | 356/445 |
| 4,680,084 | 7/1987 | Heimann et al. | 356/445 |
| 4,766,551 | 8/1988 | Begley | 356/448 |
| 4,899,055 | 2/1990 | Adams | 356/448 |

Primary Examiner—Mahshid D. Saadat
Assistant Examiner—David Ostrowski
Attorney, Agent, or Firm—Linval B. Castle

[57] ABSTRACT

The correction for scattered light reflected from a substrate having surface irregularities and the measurement of thin film thickness on that substrate are made using a spectrophotometer system and the Fresnel reflectance equation.

1 Claim, 3 Drawing Sheets

SCATTER CORRECTION IN REFLECTIVITY MEASUREMENTS

BRIEF SUMMARY OF THE INVENTION

This invention relates generally to the measurement of thin films and particularly to the problem of measuring the thickness of thin films on substrates having surface irregularities which causes the incident light to scatter when reflected from the surface.

In the semiconductor industry in particular, it is often necessary to measure film thicknesses ranging from less than one hundred Angstroms to as thick as tens of microns. When films are deposited on a smooth substrate such as silicon, reflective measurements are quite accurately made using a spectrophotometer system which collects the reflectance spectrum, and then applies standard curve-fitting methods to match the measured reflectance spectrum to a theoretical, mathematical model of reflectance.

Generally, if a film is thick enough so that its reflectance spectrum contains two or more extreme, standard curve-fitting methods are tolerant of amplitude errors between the measured sample the the theoretical model. The frequency information provided by the extrema is sufficient to provide a measurement of film thickness. However, when a film is so thin as to not have any extreme in its reflectance spectrum, it is essential to have a model which matches measured data.

When a film is deposited on a substrate having surface irregularities, the scatter of reflected light from the surface results in measured reflectance spectra which do not match any theoretical model which assumes perfect specular reflectance. Film thickness cannot be accurately determined unless the scatter is somehow modeled.

This invention provides a method for measuring the relative amount of scatter in a sample, compared to a theoretically perfect sample with no scatter, and then uses the measured scatter to adjust the theoretical reflectance model so that it matches measured samples more closely, thus permitting more accurate film thickness measurements.

BRIEF DESCRIPTION OF THE DRAWINGS

In the drawings which illustrate the preferred embodiment of the invention.

Figure 1:
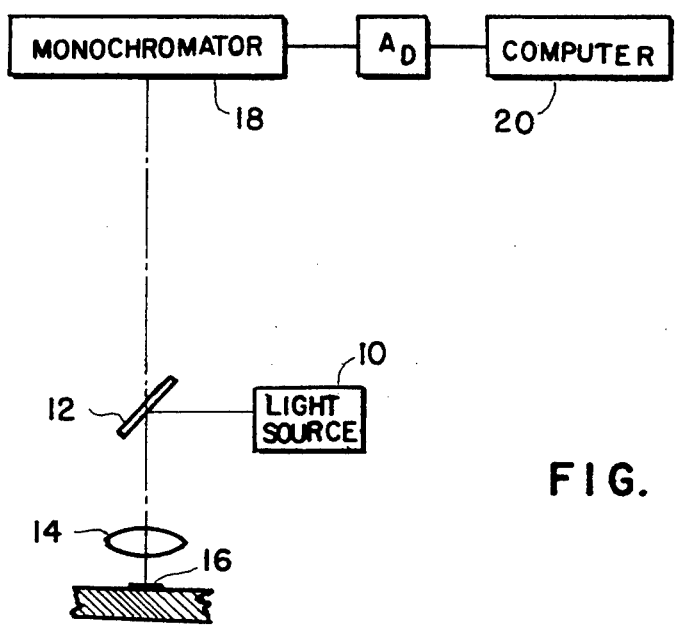
FIG. 1 illustrates a typical spectrophotometer system as used with the invention.

Illustrated in FIG. 1 is a spectrophotometer system comprising an energy source 10 for generating light of wavelength λ which is directed by a dichroic beam splitter 12 through an objective lens 14 to a sample 16. The image of the sample is then magnified by the the objective and the beam passes through the beam splitter and is focused on a monochromator 18 where the intensity of a narrow band of wavelengths is measured and is recorded by a computer 20 in its memory.

Figure 2:
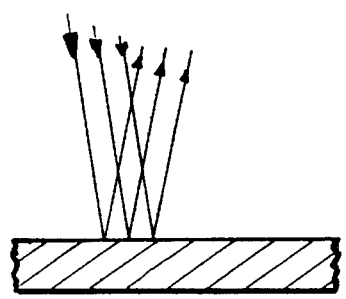
FIG. 2 illustrates light reflected from a non-scattering surface.
Figure 3:
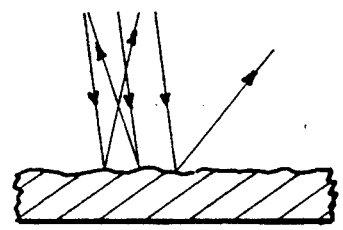
FIG. 3 illustrates light reflected from a scattering surface.
Figure 4:
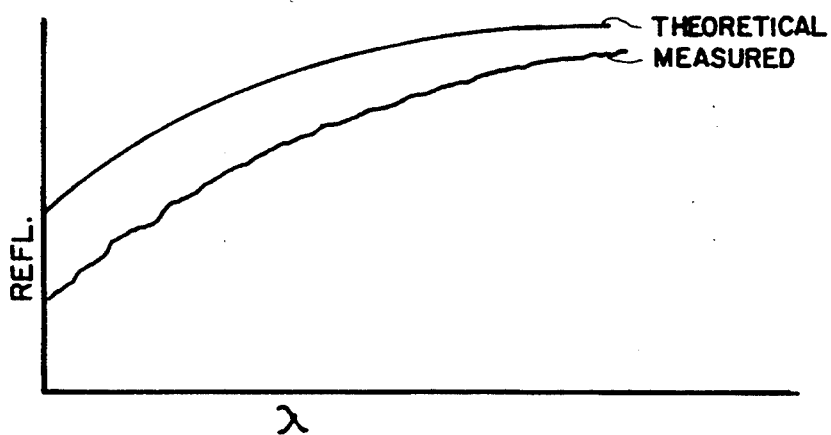
FIG. 4 illustrates curves of reflectivity from a theoretically perfect sample and from a typical measured sample.

If it were possible to deposit an absolutely smooth thin film on an absolutely smooth substrate surface, as shown in FIG. 2, measurements of reflectivity and determination of the thin film thickness would be accurate. However in practice, this is not the case and a more typical surface is illustrated in the greatly enlarged view of FIG. 3 showing scatter in the reflected beams from a film having very small surface irregularities. This scatter results in reflectance measurements which are inaccurate and do not match a theoretical model, as shown in FIG. 4. As previously mentioned, the invention provides a way to measure the relative amount of scatter and then use the measured scatter to adjust the theoretical reflectance model so that it closely matches measured samples.

Although any mathematical formula which adequately describes the theoretical reflectance of a film on a non-scattering substrate could have been used, the invention uses the following forms of the Fresnel reflectance formula to compute the theoretical model of reflectance. Given the following:

$n_I$ = complex refractive index of film
$n_0$ = complex refractive index of substrate
d = thickness of film in nanometers
λ = wavelength of incident light
φ = angle of incident light = 0 degrees
ambient medium = air Reflectance, R, is computed by:

$$r_I = (1 - n_I)/(1 + n_I) \quad (1)$$

$$r_0 = (n_I - n_0)/(n_I + n_0) \quad (2)$$

$$X = 4\pi n_I d/\lambda \quad (3)$$

$$Rho = (r_I + r_0^* \exp(i^*X))/(1 + r_I^* r_0^* \exp(i^*X)) \quad (4)$$

(note: exp (i*X) may be read as $e^{ix}$)

$$R = |Rho|^2 \quad (R = \text{magnitude squared of Rho}) \quad (5)$$

Note that $r_I$, $r_0$, X, and Rho are all complex numbers with Rho being the complex reflectance. Reflectance, R, is real.

Before the system can measure the unknown film thickness of any sample, it must take reflectance measurements of both a reference sample and a calibration sample. These measurements are then used to obtain a theoretical model of reflectance which matches measured reflectance from samples with scatter much better than a model assuming perfect specular reflectance.

Given a reference sample whose optical properties are well known and a calibration sample, the system illustrated in FIG. 1 performs the following operations at each wavelength of interest:

1. The system first computes and stores in memory the theoretical reflectance, RTr, of the reference sample. This must be a sample whose measured reflectance closely matches that of the theoretical model and may be a bare substrate or have a film on the surface of a substrate. The important requirement is that the measured reflectance of the reference sample matches the theoretical reflectance. Silicon is a good choice since much is known and has been published about the properties of silicon.

2. The system then measures and stores in memory the raw intensity, Ir, of the reference sample. All optical elements in the optical system of FIG. 1 absorb energy from the radiating source 10 thereby requiring calibration of the system. This is done by dividing the measured raw intensity of the sample by that of a known reference to normalize the data so that it is independent of the efficiencies of the various components.

3. The system of FIG. 1 then measures, computes and stores in memory the theoretical real reflectance, RTc, and the theoretical complex reflectance, RhoTc, of the calibration sample. This calibration sample should be comprised of the same film and substrate materials and have the same scatter characteristics as those samples whose unknown film thicknesses will ultimately be measured by the system. RTc and RhoTc are computed assuming no scatter.

4. The raw intensity, Ic, of the calibration sample is then measured and stored in memory.

5. Using the raw intensity data stored during operations 1, 2 and 4, above, the computer computes and stores in memory the measured real reflectance, RMc, of the calibration sample:

$$RMc = (Ic/Ir) * RTr \quad (6)$$

Note that RMc is the absolute reflectance of the calibration sample. By use of the reference sample as described above, the absolute reflectance of any unknown sample may be measured, regardless of its film and substrate composition.

Also note that the ratio RMc/RTc (from operation #3) gives the relative measure of the amount of scatter in the calibration sample compared to to an ideal non-scattering sample.

6. The computer 20 in the system of FIG. 1 then computes and stores in memory the measured complex reflectance, RhoMc, of the calibration sample.

$$RhoMc = RhoTc * \sqrt{(RMc/RTc)} \quad (Eq\ 7)$$

7. A value for RhoMc having been determined, the system then solves for $r_0$ using Eq 4.

$$r_0 = (r_f - RhoMc)/(RhoMc * r_l - 1) * (\exp(i*X)) \quad (8)$$

Figure 5:
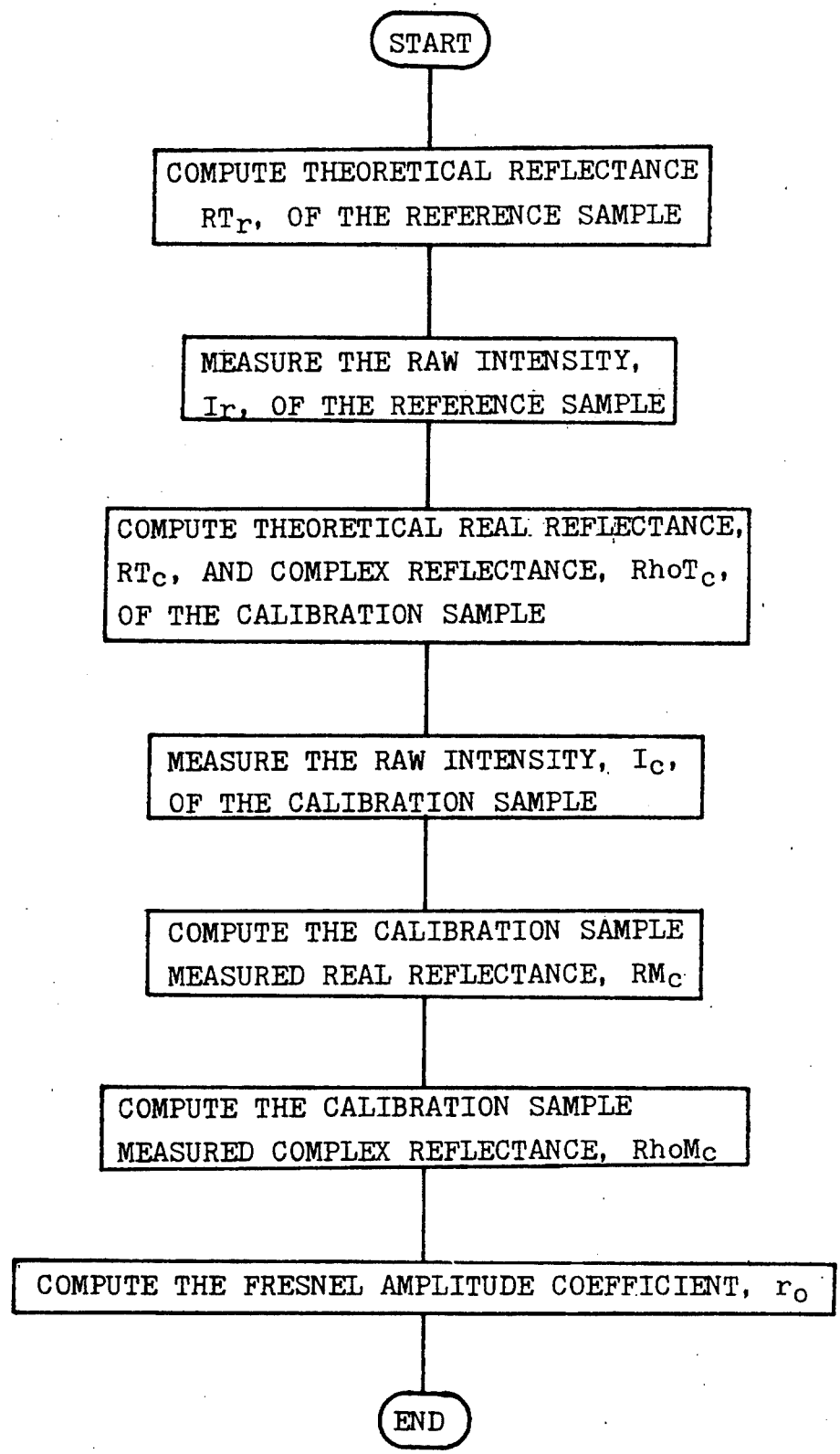
FIG. 5 is a flow diagram summarizing the procedure for measuring the reference and calibration sample.

This new value for $r_0$ represents the Fresnel amplitude coefficient which has been adjusted from its original theoretical value (from Eq 2) in order to produce a new reflectance model which accounts for scatter, and is summarized in FIG. 5. This new value for $r_0$ is stored in memory and is used in the measurements of other samples. For example, the system of FIG. 1 may make measurements that may then be used with standard curve fitting methods to determine thickness of the thin film on a substrate, a measurement that is impossible without correcting for scatter.

Figure 6:
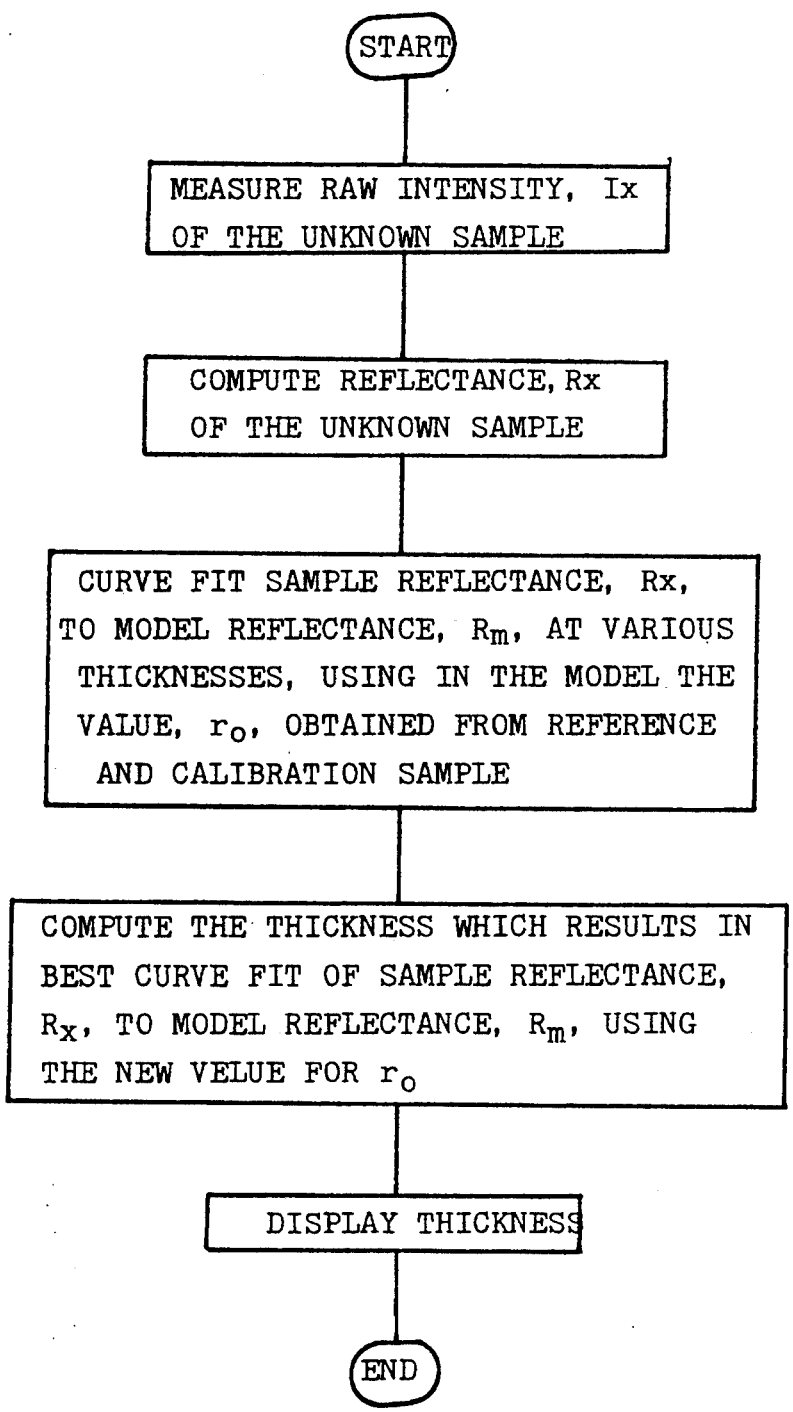
FIG. 6 is a flow diagram outlining the procedure for measuring a sample of unknown film thickness.

Having computed and stored the new adjusted value for $r_0$, the determination of the unknown film thickness is as follows and is summarized in FIG. 6.

8. The system of FIG. 1 measures and stores in memory the raw intensity, Ix, of the unknown sample.

9. The system then computes and stores in memory the unknown sample reflectance, Rx.

Rx = Ix/Ir

10. Using standard curve fitting methods, the system computes the value of film thickness which results in the best fit of the unknown sample reflectance, Rx, to the theoretical sample reflectance Rm, (from Eqs. 5 and 7). The model reflectance computation uses the new value of $r_0$, resulting in a much better fit of sample to model, compared to the fit obtained with the original value of $r_0$, and a more accurate measure of film thickness.

11. The system displays the computed value of film thickness.

I claim:

1. A method for measuring the thickness of a film on a substrate that exhibits scattering of reflected light due to surface irregularities, said method comprising the steps of:

measuring and storing the intensity of reflected light from a reference sample whose optical properties are known by the use of a spectrophotometer system and a digital computer with a memory;

measuring and storing the intensity of the reflected light from a calibration sample of known film thickness by use of the same spectrophotometer system;

computing the theoretical reflectances of the reference sample and the calibration sample by use of the computer;

computing the absolute reflectance of the calibration sample;

computing the measured complex reflectance and the Fresnel amplitude coefficient of the calibration sample;

measuring and storing the intensity of the reflected light from a sample of unknown film thickness;

computing the theoretical reflectance of the sample of unknown film thickness; and using standard curve fitting methods and said computed Fresnel amplitude coefficient, compute the value of film thickness resulting in the best curve fit of measured reflectance of the sample of unknown film thickness to the modified mathematical model of reflectance at that thickness.

* * * * *